United States Patent
Al-Jarba

(10) Patent No.: US 10,391,269 B2
(45) Date of Patent: Aug. 27, 2019

(54) NASAL SPRAYER WITH MULTIPLE APPLICATORS

(71) Applicant: Meshil A. M. O. H. Al-Jarba, Safat (KW)

(72) Inventor: Meshil A. M. O. H. Al-Jarba, Safat (KW)

( * ) Notice: Subject to any disclaimer, the term of this patent is extended or adjusted under 35 U.S.C. 154(b) by 0 days.

(21) Appl. No.: 16/179,521

(22) Filed: Nov. 2, 2018

(65) Prior Publication Data

US 2019/0160238 A1    May 30, 2019

Related U.S. Application Data

(60) Provisional application No. 62/592,000, filed on Nov. 29, 2017.

(51) Int. Cl.
| | |
|---|---|
| *A61M 15/08* | (2006.01) |
| *B05B 1/14* | (2006.01) |
| *A61M 11/00* | (2006.01) |
| *B05B 11/00* | (2006.01) |
| *A61M 31/00* | (2006.01) |
| *A61M 15/00* | (2006.01) |

(52) U.S. Cl.
CPC .......... *A61M 15/08* (2013.01); *A61M 11/006* (2014.02); *B05B 1/14* (2013.01); *B05B 11/30* (2013.01); *A61M 15/0001* (2014.02); *A61M 31/00* (2013.01)

(58) Field of Classification Search
CPC ....................................................... B05B 11/30
See application file for complete search history.

(56) References Cited

U.S. PATENT DOCUMENTS

| | | | | | |
|---|---|---|---|---|---|
| 3,398,743 | A | * | 8/1968 | Shimon Shalit | A61M 3/0262 604/181 |
| 4,944,429 | A | * | 7/1990 | Bishop | B05B 11/0027 222/153.13 |
| 5,215,227 | A | * | 6/1993 | Farner | B05B 11/3052 222/175 |

(Continued)

FOREIGN PATENT DOCUMENTS

| | | |
|---|---|---|
| CN | 103081801 A | 5/2013 |
| CN | 203226922 U | 10/2013 |

(Continued)

*Primary Examiner* — Tatyana Zalukaeva
*Assistant Examiner* — Guy K Townsend
(74) *Attorney, Agent, or Firm* — Richard C. Litman

(57) ABSTRACT

The nasal sprayer with multiple applicators is a liquid dispensing device with two separate applicators. A first applicator is in the form of a spray nozzle, similar to that of a conventional nasal sprayer, which is provided for atomized liquid dispensing to the nasal passages. A second applicator is in the form of a flexible tube, which is adapted for dispensing liquid to deeper regions, such as the Eustachian tube or the adenoid or sinus regions. The nasal sprayer with multiple applicators includes a receptacle for receiving a volume of a liquid medicament for intranasal treatment. A pump assembly selectively transfers a metered dose of the liquid medicament to a dispensing assembly for dispensing through a selected one of first and second ports. A spray nozzle is in fluid communication with the first port and a flexible spray tube is in fluid communication with the second port.

3 Claims, 5 Drawing Sheets

(56) References Cited

U.S. PATENT DOCUMENTS

| | | | | |
|---|---|---|---|---|
| 5,370,318 A | * | 12/1994 | Weston | B05B 11/0064 239/533.14 |
| 5,894,963 A | * | 4/1999 | Hirota | B05B 11/3019 222/321.2 |
| 5,906,198 A | | 5/1999 | Flickinger | |
| 5,989,217 A | * | 11/1999 | Ohki | A61M 15/0028 604/94.01 |
| 6,092,692 A | * | 7/2000 | Riskin | A61J 7/04 222/182 |
| 6,145,703 A | * | 11/2000 | Opperman | A61M 15/0065 222/82 |
| 6,173,868 B1 | * | 1/2001 | DeJonge | A61M 15/0065 222/153.13 |
| 6,269,976 B1 | * | 8/2001 | DeJonge | B05B 11/3047 222/321.7 |
| 6,516,795 B1 | | 2/2003 | Bougamont et al. | |
| 7,726,520 B2 | * | 6/2010 | Harrold | B05B 11/3015 222/162 |
| 8,360,056 B2 | * | 1/2013 | Ishizeki | A61M 15/0028 128/203.15 |
| 9,550,036 B2 | * | 1/2017 | Hoekman | A61M 11/02 |
| 2008/0081079 A1 | * | 4/2008 | Cha | A61K 33/14 424/680 |
| 2008/0178871 A1 | * | 7/2008 | Genova | A61M 15/08 128/200.23 |
| 2008/0312315 A1 | * | 12/2008 | Daniloff | A61K 9/0024 514/449 |
| 2009/0236445 A1 | * | 9/2009 | Lintern | A61M 11/00 239/483 |
| 2010/0095957 A1 | * | 4/2010 | Corbacho | A61M 15/0028 128/200.14 |
| 2010/0114016 A1 | * | 5/2010 | Gallo | A61H 35/04 604/73 |
| 2010/0199984 A1 | * | 8/2010 | Williams, III | A61M 15/0065 128/200.23 |
| 2010/0282246 A1 | * | 11/2010 | Djupesland | A61M 15/08 128/200.14 |
| 2013/0072755 A1 | * | 3/2013 | Papania | A61M 11/005 600/109 |
| 2015/0258287 A1 | * | 9/2015 | Shahaf | A61M 11/02 128/200.19 |
| 2016/0058960 A1 | * | 3/2016 | Papania | A61B 1/00195 600/103 |
| 2016/0339188 A1 | * | 11/2016 | Flickinger | A61M 15/08 |
| 2018/0133415 A1 | * | 5/2018 | Esteve | A61M 11/06 |

FOREIGN PATENT DOCUMENTS

| | | | | |
|---|---|---|---|---|
| CN | 203736522 U | | 7/2014 | |
| DE | 3929964 A1 | * | 1/1991 | A61H 35/04 |
| DE | 3929964 A1 | | 1/1991 | |
| JP | 2004129823 A | | 4/2004 | |

* cited by examiner

NASAL SPRAYER WITH MULTIPLE APPLICATORS

CROSS-REFERENCE TO RELATED APPLICATION

This application claims the benefit of U.S. Provisional Patent Application Ser. No. 62/592,000, filed on Nov. 29, 2017.

BACKGROUND

1. Field

The disclosure of the present patent application relates to intranasal liquid dispensing, and particularly to a nasal sprayer having applicators adapted for liquid dispensing to both the nasal passages and regions beyond the nasal passages, such as the Eustachian tube or the adenoid or sinus regions.

2. Description of the Related Art

Nasal sprays have a wide variety of applications, from simple hydration and irrigation of the nasal passages to intranasal delivery of various liquid medicaments. Typical nasal sprayers include a conventional bottle for receiving water, saline or a liquid medicament coupled with a pump-type sprayer. The sprayer typically uses an atomizing nozzle for delivering the liquid, intranasally, in a mist form. Although such nasal sprayers may be effective for hydration or irrigation of the nasal passages, or delivery of a medicament to the nasal passages, they are not easily adapted for delivery of a liquid to deeper application sites, such as the Eustachian tube or the adenoid or sinus regions. A variety of tube-type dispensers and applicators are available for such deep nasal delivery of liquids, however such dispensers are typically incompatible with conventional nasal sprayers. Thus, in order to apply liquid medicaments to both regions, two separate liquid dispensing devices are typically used. Thus, a nasal sprayer with multiple applicators solving the aforementioned problems is desired.

SUMMARY

The nasal sprayer with multiple applicators is a liquid dispensing device with two separate applicators. A first applicator is in the form of a spray nozzle, similar to that of a conventional nasal sprayer, which is provided for atomized liquid dispensing to the nasal passages. A second applicator is in the form of a flexible tube, which is adapted for dispensing liquid to deeper regions, such as the Eustachian tube or the adenoid or sinus regions. The nasal sprayer with multiple applicators includes a receptacle for receiving a volume of a liquid medicament, similar to the bottle or container typically associated with a conventional nasal sprayer. A cap is provided for releasably covering and sealing an open upper end of the receptacle.

The nasal sprayer with multiple applicators further includes a dispensing assembly. The dispensing assembly includes a housing, having first and second ports formed therethrough, and a valve for selectively sealing one of the first and second ports and simultaneously opening the other one of the first and second ports. A pump assembly is further provided for selectively transferring a metered dose of the liquid medicament to the dispensing assembly for dispensing through a selected one of the first and second ports. A spray nozzle is in fluid communication with the first port and a flexible spray tube is in fluid communication with the second port.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
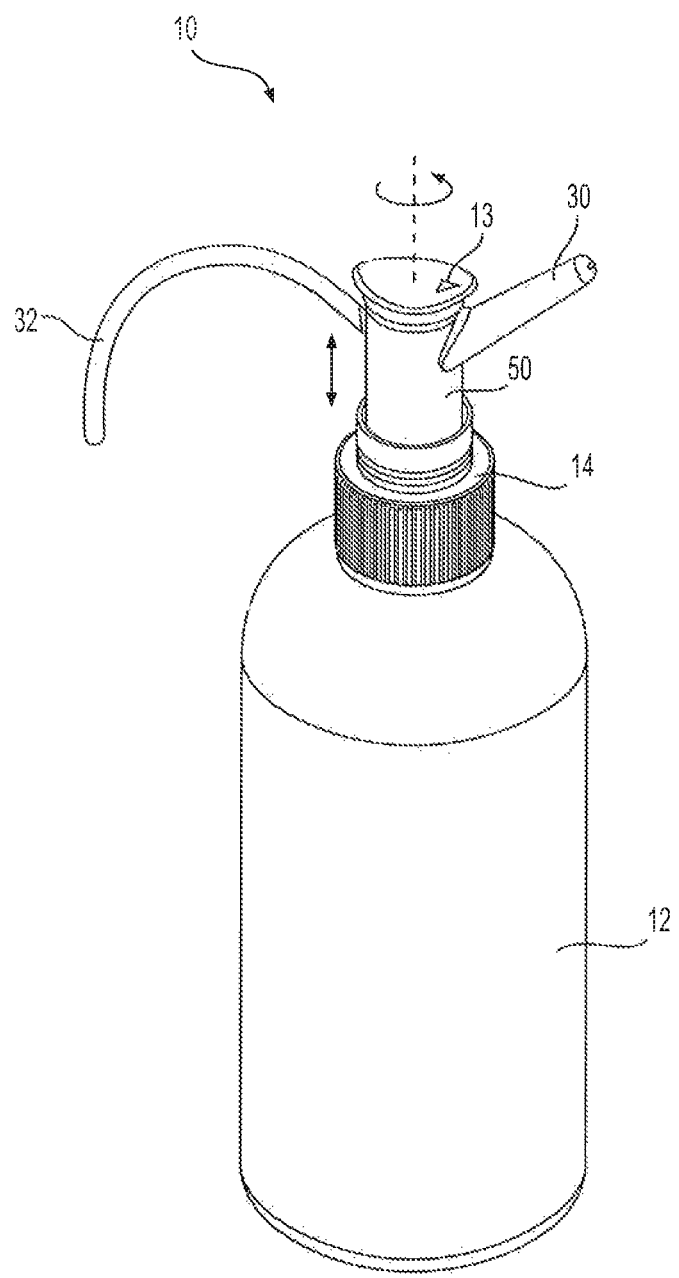
FIG. 1 is a perspective view of a nasal sprayer with multiple applicators.
Figure 2:
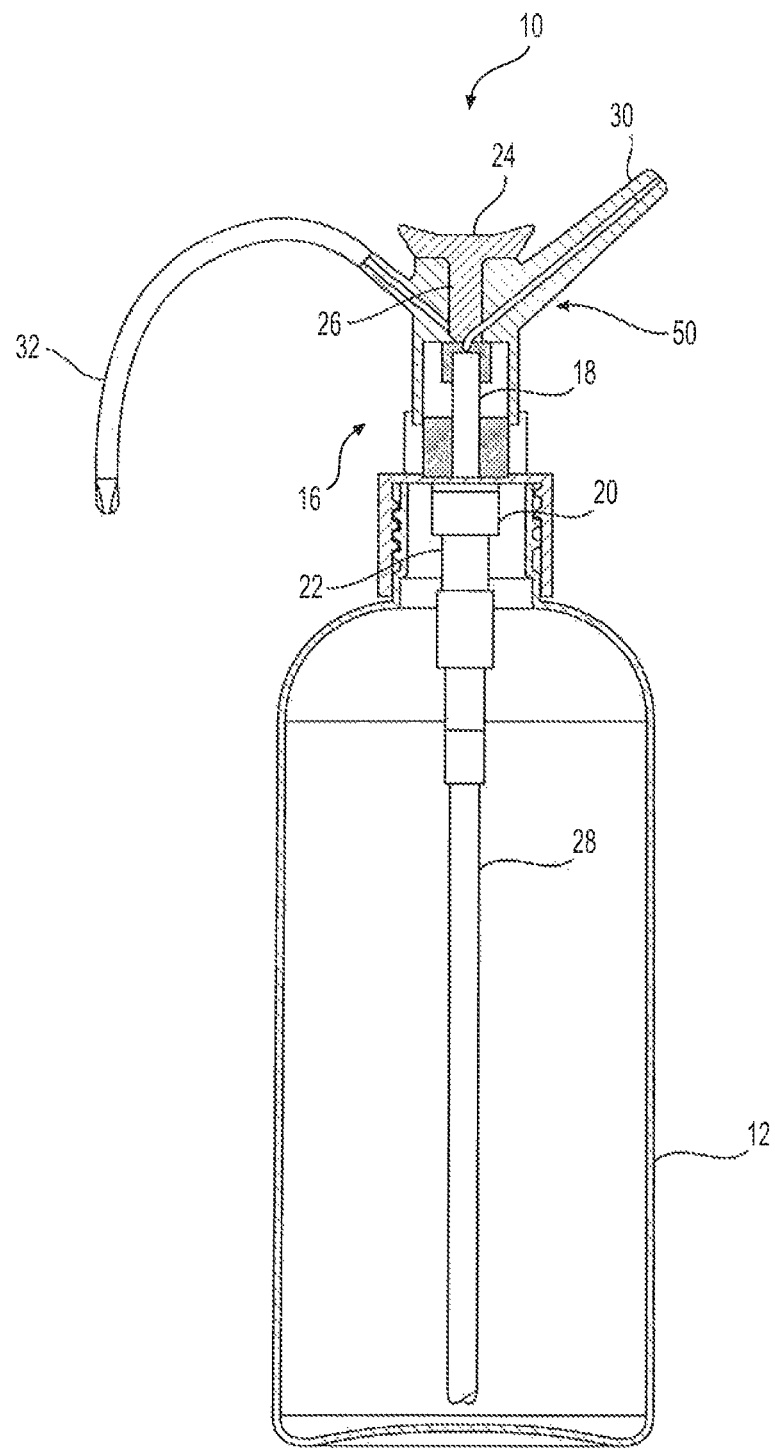
FIG. 2 is a side view in section of the nasal sprayer with multiple applicators.
Figure 3:
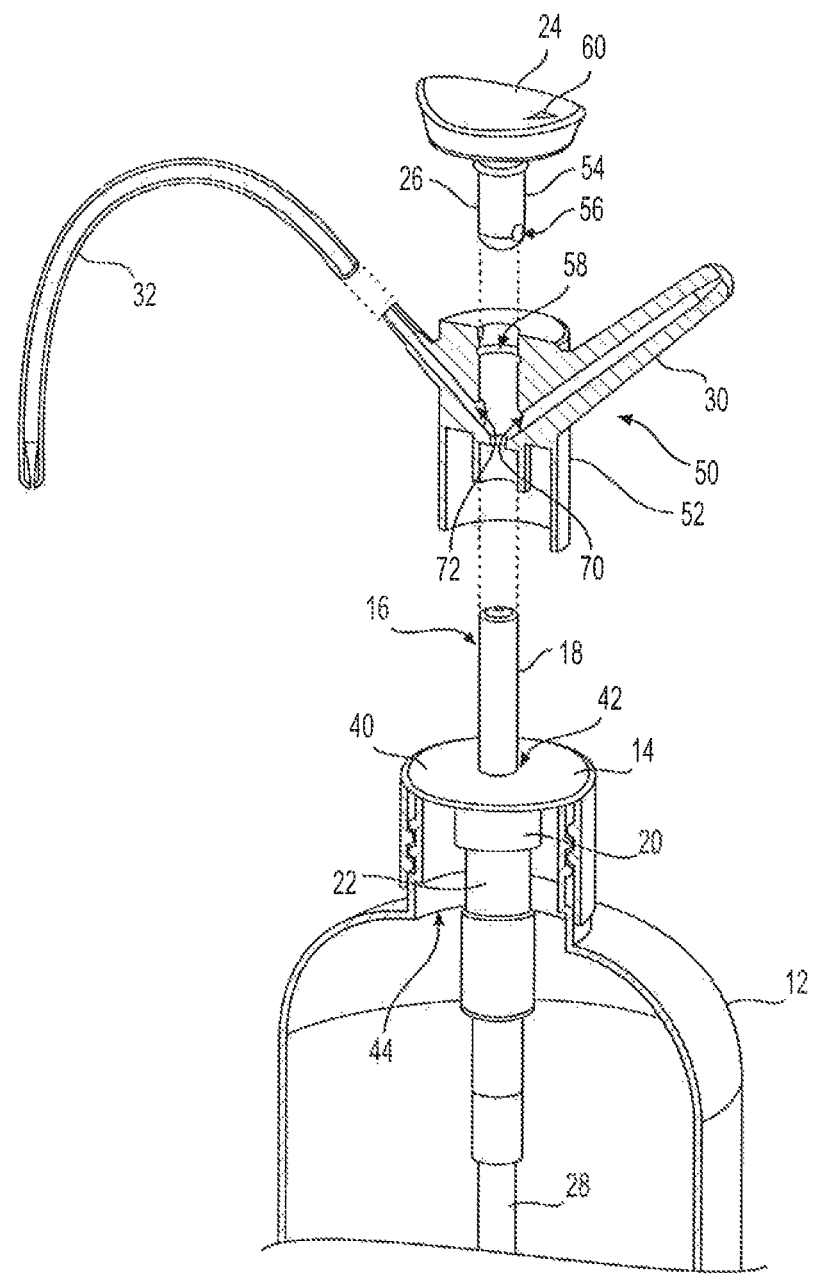
FIG. 3 is a partial, partially exploded view in section of the nasal sprayer with multiple applicators.

As shown in FIGS. 1-3, the nasal sprayer with multiple applicators 10 is a liquid dispensing device with two separate applicators. A first applicator 30 is in the form of a spray nozzle, similar to that of a conventional nasal sprayer, which is provided for atomized liquid dispensing to the nasal passages. A second applicator 32 is in the form of a flexible tube, which is adapted for dispensing liquid to deeper regions, such as the Eustachian tube or the adenoid or sinus regions. As shown, the nasal sprayer with multiple applicators 10 includes a receptacle 12 for receiving a volume of a liquid medicament, similar to the bottle or container typically associated with a conventional nasal sprayer.

A cap 14 is provided for releasably covering and sealing an open upper end 44 of the receptacle 12. Although the cap 14 is shown as having a threaded interior wall for engaging a corresponding threaded wall associated with the open upper end 44 of receptacle 12, it should be understood that cap 14 and receptacle 12 are shown for exemplary purposes only, and that receptacle 12 may be covered and sealed by any suitable type of cap, cover, wall or the like. It should be additionally understood that the overall size, shape and relative dimensions of receptacle 12 and cap 14 are shown for exemplary purposes only. Receptacle 12 may be manufactured in a variety of sizes, dependent upon the intended doses and duration of doses. For example, separate receptacles 12 may be manufactured in 150 mL, 200 mL and 250 mL sizes.

As best shown in FIG. 3, the nasal sprayer with multiple applicators 10 further includes a dispensing assembly 50. The dispensing assembly 50 includes a housing 52, having first and second ports 70, 72, respectively, formed therethrough, and a rotating valve member 26 for selectively sealing one of the first and second ports 70, 72 and simultaneously opening the other one of the first and second ports 70, 72. A pump assembly 16 is further provided for selectively transferring a metered dose of the liquid medicament to the dispensing assembly 50 for dispensing through a selected one of the first and second ports 70, 72.

As noted above, a spray nozzle 30 is in fluid communication with the first port 70 and a flexible spray tube 32 is in fluid communication with the second port 72. Flexible spray tube 32 is adapted for dispensing of the medicament to regions deeper than the nasal passages, such as the Eustachian tube or the adenoid or sinus regions. Flexible spray tube 32 may, for example, have a length on the order of about 8 cm, allowing reach to these deeper regions. Flexible spray tube 32 may be formed from any flexible, non-corrosive and non-irritating material, such as rubber, for example, with a diameter on the order of about 8 mm. Additionally, it should be understood that any suitable type of non-corrosive and non-toxic materials may be used in the construction of receptacle 12, cap 14 and spray nozzle 30, such as, for example, high density polyethylene (HDPE).

As shown in FIGS. 2 and 3, pump assembly 16 is similar to a conventional pump assembly for nasal spray bottles and the like, with a stem 18 which is selectively pressed downward through an enlarged cavity portion 20 of an adapter channel 22 by pressure exerted on upper surface 24 of rotating valve member 26. The pressure is propagated to a liquid column standing in metering tube 28, with the liquid column being subsequently forced upwardly through stem 18 to be sprayed from either nozzle 30 or flexible tube 32. As best shown in FIG. 3, similar to a conventional nasal sprayer, stem 18 is slidably received through central opening 42, which is formed through upper wall 40 of cap 14. It should be understood that the nasal sprayer with multiple applicators 10 may use any suitable type of pump assembly, such as those typically associated with nasal sprayers and similar dispensing devices, as are well known in the art.

Figure 4:
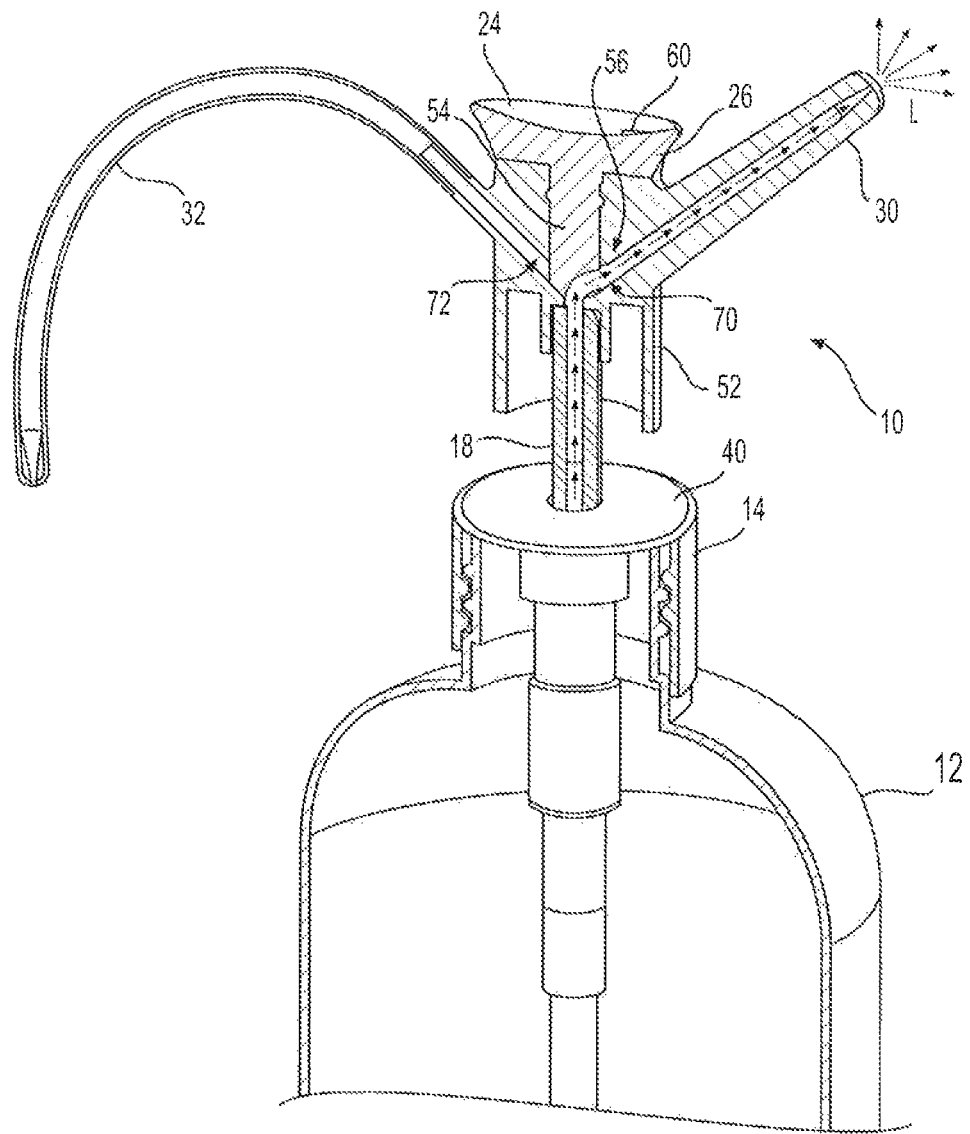
FIG. 4 is a partial view in section of the nasal sprayer with multiple applicators configured for dispensing through a first applicator.
Figure 5:
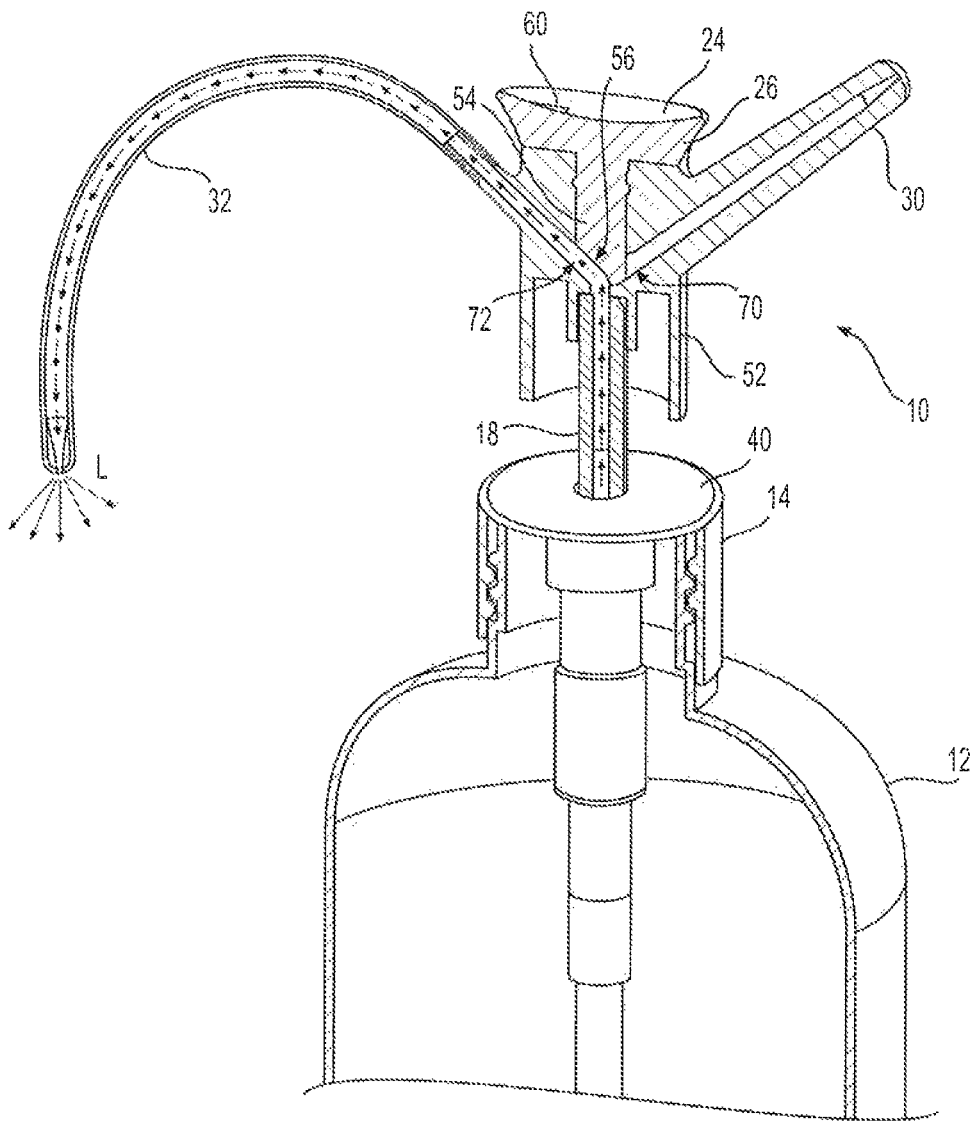
FIG. 5 is a partial view in section of the nasal sprayer with multiple applicators configured for dispensing through a second applicator.

Housing 52 of the dispensing assembly 50 has a central channel 58 formed therethrough, which is in communication with the first and second ports, 70, 72, respectively. A shaft 54 of the rotating valve member 26 is rotatably received within the central channel 58. As best seen in FIGS. 3-5, a groove 56 is formed in a lower end of the shaft 54 for providing selective fluid communication between the selected one of the first and second ports 70, 72 and the pump assembly 16.

In the configuration shown in FIG. 4, the user has rotated the rotating valve member 26 such that groove 56 allows fluid communication between stem 18 of the pump assembly 16 and first port 70. As shown in FIGS. 3 and 4, indicia 60 may be provided to visually indicate the position of the rotating valve member 26 to the user. In the position of FIG. 4, a metered dose of the liquid medicament L is allowed to flow through stem 18 and into first port 70 for dispensing through nozzle 30. As shown, when the groove 56 is positioned to allow flow through first port 70, the diametrically opposed side of shaft 54 seals the second port 72. In FIG. 5, the rotating valve member 26 is shown rotated in the opposite direction (as visually indicated by indicia 60), positioning groove 56 to allow fluid communication between stem 18 of the pump assembly 16 and second port 72. In this position, the metered dose of the liquid medicament L is allowed to flow through stem 18 and into second port 72 for dispensing through flexible tube 32. When the groove 56 is positioned to allow flow through second port 72, the diametrically opposed side of shaft 54 seals the first port 70.

It is to be understood that the nasal sprayer with multiple applicators is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A nasal sprayer, comprising:
    a receptacle for receiving a volume of a liquid medicament, the receptacle having an open upper end;
    a cap for releasably covering and sealing the open upper end of the receptacle;
    a dispensing assembly comprising:
        a housing;
        a central channel formed through the housing;
        first and second ports in fluid communication with the central channel and extending through the housing; and
        a rotating valve for selectively sealing one of the first and second ports and simultaneously opening the other one of the first and second ports, wherein the rotating valve includes a shaft, the shaft being rotatably received within a central channel, further wherein a groove is formed in a lower end of the shaft for providing selective fluid communication between the selected one of the first and second ports;
    a pump assembly for selectively transferring a metered dose of the liquid medicament to the dispensing assembly for dispensing through the groove and a selected one of the first and second ports, wherein an upper wall of the cap has a central opening formed therethrough, a stem of the pump assembly being slidably received therethrough;
    a spray nozzle in fluid communication with the first port; and
    a flexible spray tube in fluid communication with the second port;
    wherein the spray nozzle is adapted for dispensing of the metered dose to at least a first nasal passage of a user of the nasal sprayer; and
    wherein the flexible spray tube is adapted for dispensing of the metered dose to at least one of a Eustacian tube, an adenoid region, and a sinus region of a user of the nasal sprayer.

2. The nasal sprayer as recited in claim 1, wherein indicia is formed on an upper surface of the rotating valve member, the indicia being visually indicative of an angular position of the rotating valve member with respect to the housing of the dispensing assembly.

3. The nasal sprayer as recited in claim 1, wherein the pump assembly further comprises:
    an adapter channel, a lower portion of the stem being slidably received by an enlarged cavity portion thereof; and
    a metering tube in fluid communication with the adapter channel.

* * * * *